(12) United States Patent  
Agarwal

(10) Patent No.: US 8,808,768 B2  
(45) Date of Patent: Aug. 19, 2014

(54) **DEVELOPMENT OF BIOCHEMICALLY STANDARDIZED EXTRACTS FROM FRESH RHIZOMES OF TURMERIC (*CURCUMA LONGA*) FOR TREATMENT OF DISEASES CAUSED BY HYPERURICEMIA**

(76) Inventor: Kailash Chandra Agarwal, Durham, NC (US)

( * ) Notice: Subject to any disclaimer, the term of this patent is extended or adjusted under 35 U.S.C. 154(b) by 527 days.

(21) Appl. No.: 12/460,474

(22) Filed: Jul. 20, 2009

(65) Prior Publication Data

US 2010/0015260 A1    Jan. 21, 2010

Related U.S. Application Data

(60) Provisional application No. 61/135,482, filed on Jul. 21, 2008.

(51) Int. Cl.  
*A61K 36/9066*    (2006.01)

(52) U.S. Cl.  
USPC ............................... 424/756; 424/725

(58) Field of Classification Search  
USPC ............................... 424/756, 725  
See application file for complete search history.

(56) References Cited

U.S. PATENT DOCUMENTS

2003/0186998 A1*  10/2003  Marban ................. 514/262.1  
2005/0191375 A1*   9/2005  Babish et al. ............ 424/778  
2007/0280888 A1*  12/2007  Fujikawa et al. ........ 424/9.71

FOREIGN PATENT DOCUMENTS

CN    101181249 A  *  5/2008

OTHER PUBLICATIONS

Ghoneim et al. Protective Effects of Curcumin Against Ischaemia/Reperfusion Insult in Rat Forebrain; Pharmacological Research (2002), 46(3), 273-279.*

Liu et al. Antiangiogenic Effect of Curcumin in Pure Versus in Extract Forms; Pharmaceutical Biology, 2008; vol. 46, Nos. 10-11, pp. 677-682.*

* cited by examiner

*Primary Examiner* — Patricia Leith

(57) ABSTRACT

The present invention demonstrates the ethanol extracts of fresh rhizome of turmeric (*Curcuma longa*) strongly inhibit xanthine oxidase, a key biological enzyme responsible for the production of uric acid and superoxide radicals. The dose-response data demonstrate the turmeric extracts prepared with 40% and 50% ethanol are much stronger inhibitors of xanthine oxidase than curcumin. Based on the enzyme-inhibitory data ($IC_{50}$ values), a biochemical method is developed to standardize turmeric extracts/products as Enzyme-Inhibitory Units (EIU), which has many commercial and biological applications, including, identification and development of pharmacologically effective turmeric products; use of turmeric extracts/products with EIU values >50 per mg to prevent the production of harmful uric acid and superoxides in diseases caused by hyperuricemia and gout; determination of the stability (shelf-life) of turmeric products stored at the retail stores by comparing their EIU values.

8 Claims, 6 Drawing Sheets

Enzyme Inhibitory Units (EIU): EIU/mg of Extracts (solid-form)

Figure 1: Dose-Response Inhibition of Xanthine Oxidase
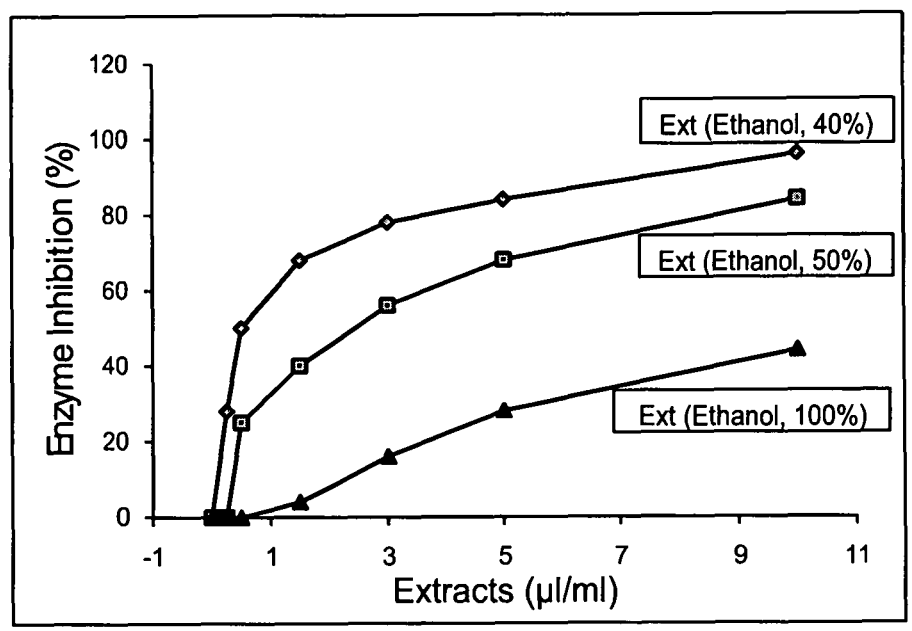
IC$_{50}$ Values
1. Extract (40% Ethanol): 0.5 µl/ml or 3.4 µg/ml
2. Extract (50% Ethanol): 2.5 µl/ml or 17.1 µg/ml
3. Extract (100% Ethanol): > 10 µl/ml or > 25 µg/ml

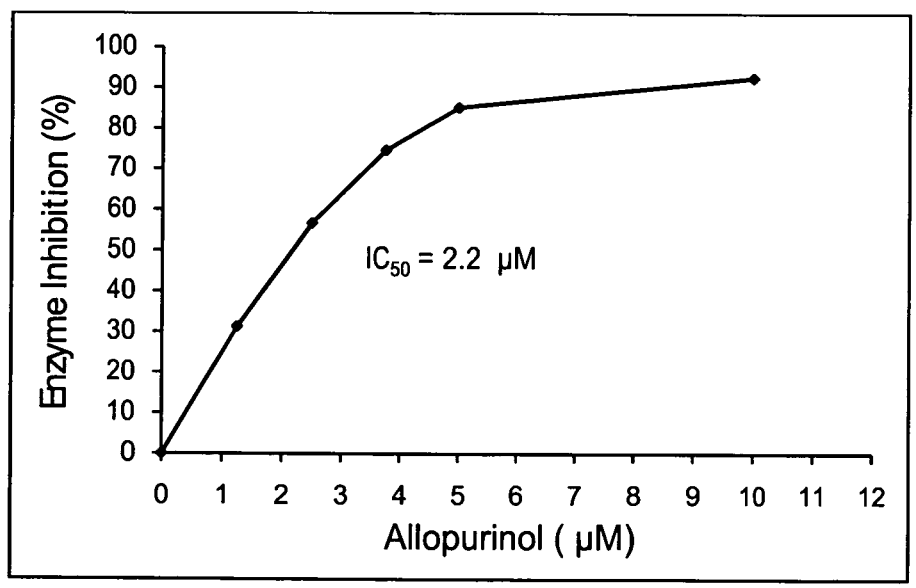
Figure 2: Xanthine Oxidase Inhibition by Allopurinol

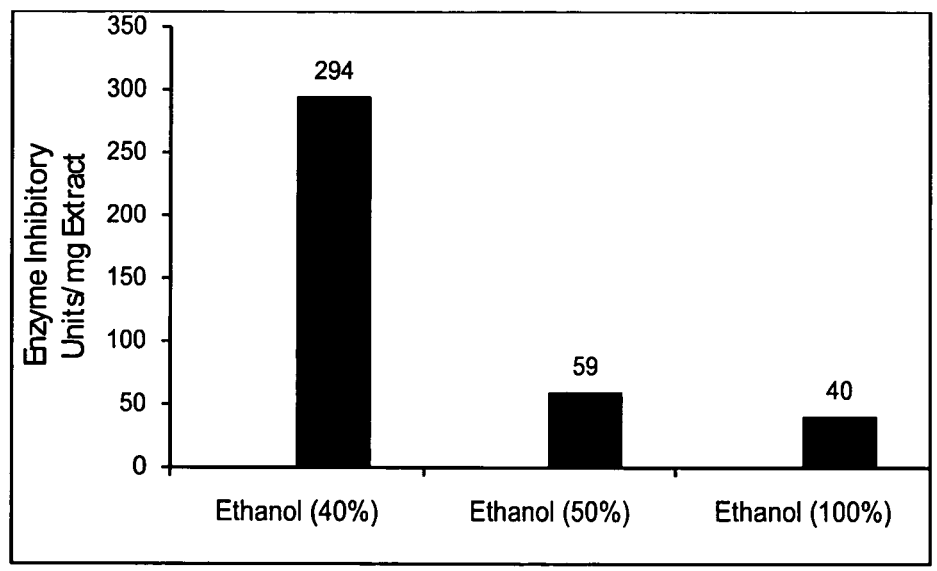
Figure 3: Enzyme Inhibitory Units/mg of Extract
(Extraction with 40%, 50%, or 100% Ethanol)
Enzyme Inhibitory Units (EIU): EIU/mg of Extracts (solid-form)

Figure 4: Enzyme Inhibitory Units/gram of original turmeric powder
(Extraction with 40%, 50%, or 100% Ethanol)
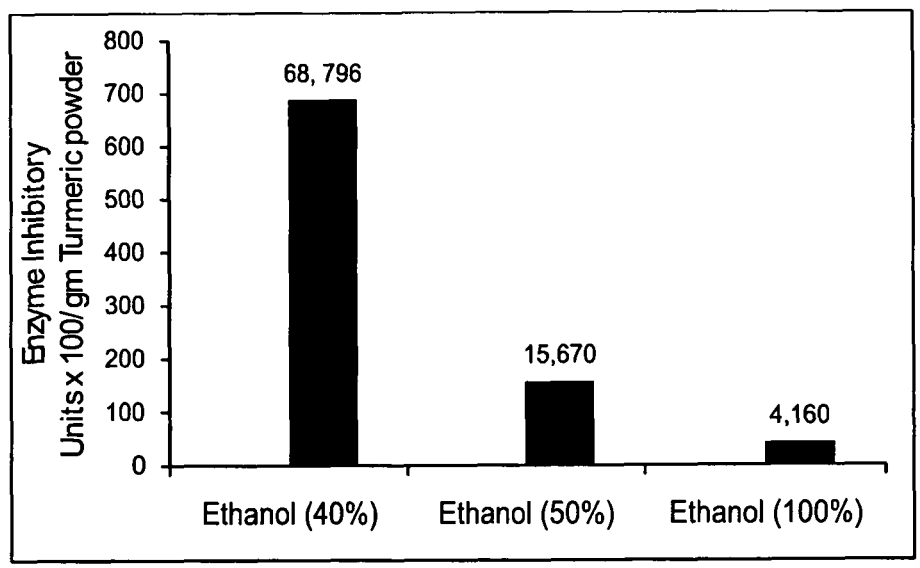
Enzyme Inhibitory Units (EIU): Recovery of EIU/gm of turmeric powder Figure 5: Effect of curcumin on xanthine oxidase activity
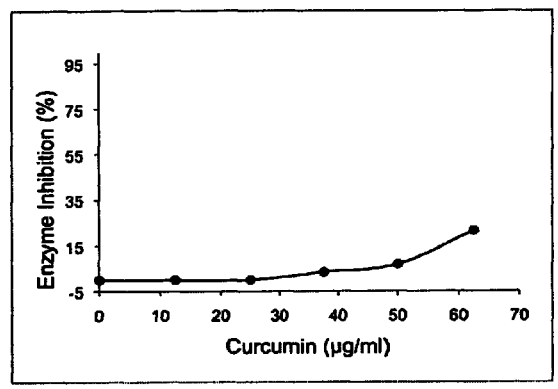
Curcumin $IC_{50}$ > 60 µg/ml Figure 6: Curcumin concentrations in turmeric ethanol extracts
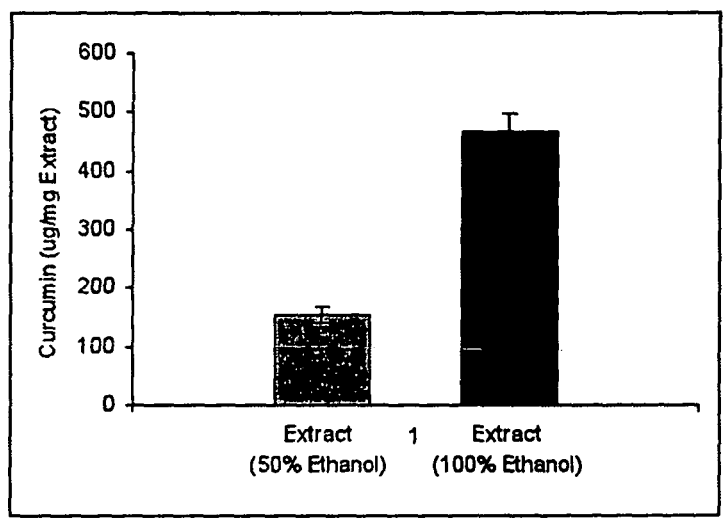
Curcumin concentrations:
Ethanol extract (50%): 153 ± 14 µg/mg
Ethanol extract (100%): 468 ± 30 µg/mg

US 8,808,768 B2

DEVELOPMENT OF BIOCHEMICALLY STANDARDIZED EXTRACTS FROM FRESH RHIZOMES OF TURMERIC (*CURCUMA LONGA*) FOR TREATMENT OF DISEASES CAUSED BY HYPERURICEMIA

This application is being filed on Jul. 20, 2009, as a PCT International Patent Application in the name of Kailash Chandra Agarwal, a citizen of the U.S., applicant for the designation of the U.S. only, and claims priority to U.S. Provisional Patent Application Ser. No. U.S. 61/135,482 filed Jul. 21, 2008.

FIELD OF INVENTION

The present invention pertains to methods for turmeric (*Curcuma longa*) rhizome extraction, biochemical standardization of powders and extracts, and their uses thereof.

BACKGROUND

Turmeric (*Curcuma longa*) is a perennial rhizomatous shrub native to southern Asia, extensively cultivated in all parts of India. Turmeric is a member of the ginger family (Zingiberaceae). The history of the use turmeric powder and its medicinal applications has been described previously, but not limited to following: internally as a tonic, blood purifier, and externally prevention and treatment of skin diseases. Turmeric also has a long history of use for its anti-inflammatory and anti-arthritic effects.

The exposure of people worldwide to turmeric compounds including curcumin, and their many uses, has led to studies aimed at elucidating some of its medicinal properties. Some important work in relation to turmeric compound, curcumin is listed in the following publications: (Kapoor L D. CRC Hand book of ayurvedic medicinal plants. Boca Raton: CRC Press, 149-150, 1990; Kunchandy E., Rao M. N. A. Oxygen radical scavenging activity of curcumin. Int J Pharm. (Amst.), 58: 237-240, 1990; Reddy A. C., Lokesh B. R. Studies on the inhibitory effects of curcumin and eugenol on the formation of reactive oxygen species and the oxidation of ferrous iron. Mol Cell Biochem., 137: 1-8, 1994; Ruby A. J., Kuttan G., Babu K. D., Rajasekharan K. N., Kuttan R. Anti-tumour and antioxidant activity of natural curcuminoids. Cancer Lett. 94: 79-83, 1995; Sreejayan N., Rao M. N. Curcuminoids as potent inhibitors of lipid peroxidation. J. Pharm Pharmacol., 46: 1013-1016, 1994; Thamlikitkul V, et al. Randomized double blind study of *Curcuma* domestica Val. For dyspepsia. J Med Assoc Thai. 72: 613-620, 1989; Polasa K, Raghuram T C, Krishna T P, Krishnaswamy. Effect of turmeric on urinary mutagens in smokers. Mutagenesis. 7: 107-109, 1992); Cheng A. L., Hsu C. H., Lin J. K., Hsu M. M., Ho Y. F., Shen T. S., Ko J. Y., Lin J. T., Lin B. R., Ming-Shiang W., et al Phase I clinical trial of curcumin, a chemopreventive agent, in patients with high-risk or pre-malignant lesions. Anticancer Res., 21: 2895-2900, 2001).

These and other experimental clinical studies have shown the beneficial effects in skin diseases, muscle pain, would-healing and cancer etc. However, the mechanism of action that can explain turmeric's therapeutic effects is not well understood. Furthermore, there is currently no available method of biochemically standardizing turmeric powder or extracts.

What is needed is a method of standardizing preparations of turmeric powder or extracts based on its biochemical mechanism of action in order to produce uniform compositions and formulations for therapeutic uses.

SUMMARY OF THE INVENTION

The present invention is directed to various methods for inhibiting the enzyme xanthine oxidase by the administration of standardized extracts of turmeric (*Curcuma longa*) powder. The standardized extracts have a potency that is determined to be approximately equivalent to what is described in more detail herein as at least one enzyme inhibitory unit, wherein each enzyme inhibitory unit is equivalent to the concentration of the extracted turmeric powder in solution that inhibits xanthine oxidase activity by 50%. The standardized turmeric preparations which inhibit xanthine oxidase activity can be used as described herein in therapeutic amounts to decrease blood uric acid levels in hyperuricemia patients.

The present invention also provides methods for preventing the degradation of hypoxanthine into oxidation products by administering effective amounts of a standardized extract of turmeric powder. By preventing the degradation of hypoxanthine into oxidative by-products, standardized extract of turmeric powder can be used to prevent tissue damage to the heart or brain during the heart or stroke attacks in ischemic heart patients.

The present invention further provides a method for the biochemical standardization of turmeric powder preparations. The turmeric powder is extracted with water-ethanol mixture and the amount of extract that inhibits xanthine oxidase activity by 50% is determined. This amount of extract is then set to be equivalent to one Enzyme Inhibitory Unit (EIU) of turmeric extract.

BRIEF DESCRIPTION OF THE FIGURES

FIG. 1 depicts the inhibition of xanthine oxidase by extracts of turmeric powder. The half maximal inhibitory concentration of turmeric powder extracted by ethanol 40%, ethanol 50% or ethanol 100% is the concentration of a turmeric extract that is required for 50% inhibition of the enzyme.

FIG. 2 depicts 50% inhibition of xanthine oxidase by the drug allopurinol presently used in decreasing blood uric acid levels.

FIG. 3 depicts biochemically standardized extracts as Enzyme Inhibitory Units (EIU) per mg of extracts of turmeric powder. The EIUs values are shown as a product of the type of extraction used: ethanol 40%, ethanol 50%, or ethanol 100%.

FIG. 4 depicts standardized extracts as Enzyme Inhibitory Units (EIU) per gram of the turmeric powder. Depicted are the numbers of EIUs multiplied by 100 per gram of turmeric powder extracted with ethanol 40%, ethanol 50%, or ethanol 100%.

FIG. 5 depicts the inhibition of xanthine oxidase by curcumin. The half maximum inhibitory concentration of curcumin that is required for 50% inhibition ($IC_{50}$) of the enzyme.

FIG. 6 depicts the concentrations of curcumin in 50% and 100% ethanol extracts of turmeric powder. Curcumin concentrations were determined by a high-pressure liquid chromatographic method and presented as µg/mg of extracts.

DETAILED DESCRIPTION OF THE INVENTION

The current invention pertains to methods for standardizing a turmeric powder extract based upon its biochemical ability to inhibit xanthine oxidase activity. The invention also provides in various embodiments, methods of using the standardized extracts to treat diseases caused by an increase of blood uric acid levels (hyperuricemia) and superoxide radicals. The invention also provides in various embodiments, methods of using the standardized extracts to prevent tissue damage due to increased production of superoxide radicals as seen during the heart attack or stroke in ischemic artery diseases.

Extraction and Standardization Procedures

In one embodiment, the invention provides methods of standardizing an extract of turmeric powder based on its mechanism of action of inhibiting xanthine oxidase. First, extracts are prepared from turmeric powder. Fresh turmeric (*Curcuma longa*) rhizomes can be obtained from any suitable commercial source such as, Indian grocery stores. Rhizomes are washed with distilled water and removed most of the rhizome skin. It is then cut into small pieces, dried at low temperature (40-42° C.), and powdered. Extracts are prepared from the dried turmeric powder using a suitable solvent. Suitable solvents can include, but are not limited to ethanol (40% in water, 50% in water or 100%).

The turmeric powder and solvent are typically combined in a ratio of 1:5 (powder:solvent) to 1:100. Preferably, powder and solvent are combined in a ratio of 1:20 to 1:80. More preferable, powder and solvent are typically combined in a ratio of 1:30-1:50. Most preferable, powder and solvent are typically combined in a ratio of 1:40. The powder and solvent can be combined using normal laboratory conditions. The subsequent solution can be optionally centrifuged in order to produce a clear extract. Clear extracts are preferred. The amount of the dissolved turmeric powder per ml of each extract is determined by drying an aliquot of the extract under controlled conditions.

Standardization of the extracts obtained from the turmeric powder can be accomplished using any available xanthine oxidase test or assay available. These include the xanthine oxidase enzyme-spectrophotometeric assay. Dose-responses are obtained and the $IC_{50}$ values determined by the appropriate technique based upon the assay used. The $IC_{50}$ values represent the amount of the extract, µl (extract) or µg (dried-form of extract) per ml of the reaction mixture, producing a 50% enzyme inhibition.

Biochemical Standardization of Turmeric Powder and Extracts

The standardization of the powder or extracts is typically carried out as the Enzyme Inhibitory Units (EIU) per mg of the dried-form of the extract or per gram of the turmeric powder. Typically, the $IC_{50}$ values are utilized for determination of Enzyme Inhibitory Units (EIU). The $IC_{50}$ value is equal to 1 EIU. Depending on the solvent used in the extraction process, the EIU values represent the potency of the extracts. A preferable and potent extract solvent is ethanol 50%. A most preferable and potent extract solvent is ethanol 40%.

Therapeutic Uses

The standardized solvent extracts described herein can be utilized in a therapeutically effective amount in a host to treat, alleviate or prevent a disease condition. The term "therapeutically effective amount" refers to an amount of a solvent extract, expressed as EIUs effective to "prevent," "alleviate" or "treat" a disease or disorder in a subject or mammal. Generally, alleviation or treatment of a disease or disorder involves the lessening of one or more symptoms or medical problems associated with the disease or disorder. "Treating" or "treatment" or "alleviation" refers to both therapeutic treatment and prophylactic or preventative measures, wherein the object is to prevent or slow down (lessen) the targeted pathologic condition or disorder.

"Treating" or "treatment" or "alleviation" refers to both therapeutic treatment and prophylactic or preventive measures, wherein the object is to prevent or slow down (lesson) the targeted pathologic condition or disorder.

In addition, the standardized turmeric extracts, by inhibiting xanthine oxidase, will prevent degradation of hypoxanthine and xanthine into harmful uric acid, superoxide radicals and hydrogen peroxide which can cause cell injury. Thus, preventing the production of these harmful degradation products will protect the host or subject from hyperuricemia and diseases caused by hyperuricemia.

Administration of an intravenous bolus of the standardized turmeric extract of the current invention to humans may transiently slow down the production of uric acid and superoxide free radicals that can cause gout, kidney stones, urate nephropathy, and ischemic heart disease.

Ischemia and reperfusion impair the inherent capacity of the heart to protect itself from related pathophysiologic events by reducing endogenous oxygen radical scavengers and inhibitors. However, other endogenously produced agents, for example, superoxide radicals are produced during ischemia, reperfusion, or both. Inhibition of xanthine oxidase by a suitable turmeric extract can have several cardioprotection actions particularly anti-neutrophil effects and inhibition of endothelial-neutrophil interactions, which are key initial steps in ischemic-reperfusion injury. The standardized turmeric extracts of the current invention may be given before or in conjunction with cardioplegia solutions to provide a potent therapeutic approach against surgical or other ischemic or reperfusion injury.

Thus, the standardized turmeric extracts of the current invention can be used to alleviate, treat or prevent conditions including but not limited to: hyperuricemia, gout, kidney stones, ischemic heart disease, and any other diseases caused by hyperuricemia.

One skilled in the art would understand that the standardized turmeric extracts of the current invention may be formulated in a wide variety of oral administration dosage forms and carriers. Oral administration can be in the form of tablets, coated tablets, hard and soft gelatin capsules, solutions, emulsions, syrups, or suspensions. The standardized turmeric extracts of the current invention can be efficacious when administered by suppository administration, among other routes of administration. The most convenient manner of administration is generally oral using a convenient daily dosing regimen which can be adjusted according to the severity of the disease and the patient's response to the medication.

It is also possible to formulate the standardized turmeric extracts of the current invention together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as suspensions, emulsions, or filled capsules for oral use; or in the form of suppositories for rectal or vaginal administration. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the desired dose and pharmacokinetic parameters.

The term "excipient" as used herein refers to a compound that is used to prepare a pharmaceutical composition, and is generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

Solid form preparations include powders, tablets, pills, capsules, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, methylcellulose, sodium carboxymethylcellulose, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs and aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous suspensions can be prepared by dispersing the finely divided active component in water with viscous material, such as natural or synthetic gums, resins, methylcellulose, sodium carboxymethylcellulose, and other well known suspending agents.

Suitable formulations along with pharmaceutical carriers, diluents and expcipients are described in *Remington: The Science and Practice of Pharmacy* 1995, edited by E. W. Martin, Mack Publishing Company, 19th edition, Easton, Pa., which is hereby incorporated by reference. A skilled formulation scientist may modify the formulations within the teachings of the specification to provide numerous formulations for a particular route of administration without rendering the compositions of the present invention unstable or compromising their therapeutic activity.

The modification of the present extracts to render them more soluble in water or other vehicle, for example, may be easily accomplished by minor modifications (e.g., salt formulation), which are well within the ordinary skill in the art. It is also well within the ordinary skill of the art to modify the route of administration and dosage regimen of a particular compound in order to manage the pharmacokinetics of the present compounds for maximum beneficial effect in patients.

Another embodiment of the present invention is directed to a use of the standardized turmeric extracts in the manufacture of a medicament for the treatment of any of the conditions disclosed herein.

The term "medicament" means a substance used in a method of treatment and/or prophylaxis of a subject in need thereof, wherein the substance includes, but is not limited to, a composition, a formulation, a dosage form, and the like, comprising the standardized turmeric extracts of the current invention. It is contemplated that the standardized turmeric extracts of the current invention can be utilized either alone or in combination with another drug or compound.

The term "subject" means a mammal, which includes, but is not limited to, cattle, pigs, sheep, chicken, turkey, buffalo, llama, ostrich, dogs, cats, and humans, preferably the subject is a human.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. One of ordinary skill in treating diseases described herein will be able, without undue experimentation and in reliance on personal knowledge, experience and the disclosures of this application, to ascertain a therapeutically effective amount of the compounds of the present invention for a given disease and patient.

When the treatment is combination therapy, "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

The following methodology was employed in discovering the above invention, listed here as examples.

EXAMPLES

Example 1

Extraction of Turmeric Powder

Preparation of extracts from fresh turmeric rhizome powder: Extracts are prepared using ethanol (40%), ethanol (50%), or ethanol (100%) in a ratio 1:40 (powder:solvent) by constant gentle stirring at room temperature. Experiments outlined here have used 0.25 gm turmeric powder and 10 ml of the solvent for each extraction. After 20 hours of gentle stirring, each extract is centrifuged for 30 min at 12,000 rpm to remove insoluble turmeric residue. Clear extracts are collected and used in studies described below. The amount of the dissolved herb per ml of each extract is determined by drying an aliquot (4 ml) of the extract at 40-42° C. overnight in a temperature-controlled oven. The dried contents are 5.85, 6.64, and 2.60 mg/ml of 40% ethanol, 50% ethanol, and 100% ethanol extracts respectively.

Example 2

Hypoxanthine Production and Xanthine Oxidase Enzyme Assay

The cellular adenosine 5'-triphosphate (ATP) is enzymatically converted into hypoxanthine. The common pathway for production of hypoxanthine involves: ATP>>ADP>>AMP>>Adenosine>>Inosine>>Hypoxanthine.

Xanthine oxidase is the key enzyme that catalyzes the following reactions with the formation of uric acid, hydrogen peroxide, and oxygen free radicals.

Hypoxanthine+$O_2$+$H_2O$→Xanthine+$H_2O_2$+$O_2^-$.

Xanthine+$O_2$+$H_2O$→UricAcid+$H_2O_2$+$O_2^-$.

The turmeric extracts as obtained above are used to examine the effects on xanthine oxidase activity. Xanthine oxidase assay involves measurement of enzymatic conversion of hypoxanthine into uric acid, which is measured spectrophotometerically. The assay is performed in 50 mM Tris-HCl buffer (pH 8.0) containing 50 μM hypoxanthine. After incubation at 25° C. for 2-3 min, the enzymatic reaction is initiated by addition of an appropriate amount of xanthine oxidase purchased from Sigma Chemical Company, St Louis, Minn. The enzyme activity is calculated from the increase in absorbency at 293 nm. One unit of xanthine oxidase activity is the amount of the enzyme that catalyzes 1 μmole of hypoxanthine/min/mi of the reaction mixture ($\epsilon_M$=1.25×$10^4$).

Example 3

Inhibition of Xanthine Oxidase

The $IC_{50}$ values have been determined by examining the dose-response effects of the extracts. The $IC_{50}$ values represent the amount of the extract, μl (extract) or μg (dried-form of extract) per ml of the reaction mixture, producing the enzyme inhibition by 50%. In the enzyme assay, first a background reading is recorded on the chart for 1-2 min, followed by the addition of an appropriate amount of the enzyme to start the reaction, and the production of uric acid is monitored at 293 nm as above. The amount of the extract added to the reaction mixture depends on the enzyme inhibition. Normally, various amounts of the enzyme are selected, which give the enzyme inhibition from 10% to about 100%. FIG. 1 shows the $IC_{50}$ values, which are determined from the dose-response effects of the turmeric extracts on xanthine oxidase. The extract prepared with 40% ethanol shows a much stronger inhibition of xanthine oxidase ($IC_{50}$, 3.4 μg/ml) as compared to 50% ethanol ($IC_{50}$, 17.1 μg/ml) or 100% ethanol ($IC_{50}$, >25 μg/ml). These studies suggest that the active principle with a strong xanthine oxidase-inhibiting activity can be most effectively extracted with 40% ethanol.

Example 4

Biochemical Standardization of Turmeric Powder and Extracts

The standardization of the powder or extracts was carried out as xanthine oxidase Enzyme Inhibitory Units (EIU) per mg of the dried-form of the extract or per gram of the turmeric powder. The $IC_{50}$ values were employed for determination of Enzyme Inhibitory Units (EIU). The $IC_{50}$ value is equal to 1 EIU. For example, using the data from our experiments with turmeric extracts, we have estimated EIU values of 294, 59, and <40 per mg of the extracted turmeric for 40% ethanol, 50% ethanol, and 100% ethanol extracts respectively (FIG. 3). Similarly, FIG. 4 represents the biochemical-standardized values as EIU/gm of the original turmeric powder. Depending on the solvent used in the extraction process, the EIU values represent the potency of the extracts. For example, the extract prepared with 40% ethanol gives the most potency of the extract (EIU of 68,796) as compared to the EIU of 15,670 with 50% ethanol extract, or EIU of <4,160 or less with 100% ethanol extract. The recovery of the active fraction with EIU/gm of turmeric powder is highest in the 40% ethanol extract.

Table 1 summarizes the data obtained from above experiments with turmeric powder. Based on these findings if we employ 1 Kg the turmeric powder and use 40% ethanol for extraction, one can anticipate approximately 234 gm (23.4%) of the solid-form of the extract containing about 294 EIU/mg (or 294,000 EIU/gm) of the extract, or 68,800 EIU/gm 4 of the original turmeric powder. Estimation of EIU values for a particular extract is an excellent tool to standardize the extract biochemically. In addition, the EIU values will assist us in examining the biochemical activity of the extract during the storage (Shelf-Life).

TABLE 1

Summary Data: Turmeric Extraction, $IC_{50}$ and EIU Values

| | Solvent Composition for Extraction | | |
|---|---|---|---|
| Experimental | Ethanol, 40% | Ethanol, 50% | Ethanol, 100% |
| Herb powder, 0.25 gm | 10 ml | 10 ml | 10 ml |
| Dissolved herb/ml | 5.85 mg | 6.64 mg | 2.60 mg |
| % Dissolved | 23.4% | 26.6% | 10.4% |
| $IC_{50}$ value for XO | 3.4 μg/ml | 17.1 μg/ml | >25 μg/ml |
| Inhibitory Units[1] | 294/mg | 59/mg | <40/mg |
| Inhibitory Units[2] | 68,796/gm | 15,670/gm | <4,160/gm |

[1]Enzyme Inhibitory Units/mg of extracted solid-form of the extracts
[2]Enzyme Inhibitory Units/gm of the original turmeric powder These embodiments or examples should be considered to be non-limiting and are presented to illustrate just a few of the possibilities of the compositions and methods of the present invention. While the principles of this invention have been described in connection with specific embodiments, it should be clearly understood that these descriptions are made only by way of example and are not intended to limit the scope of the invention. As such, the present invention may be embodied in other specific forms without departing from the spirit or essential attributes thereof, and, accordingly, reference should be made to the appended claims, rather than to the foregoing specification as indicating the scope of the invention.

All the references contained herein are hereby incorporated by reference in so far as needed to supplement the present disclosure.

What is claimed is:

1. A method for treating gout or hyperuricemia comprising:
    orally administering to a subject having gout or hyperuricemia, an effective amount of a pharmaceutical dosage form, wherein said pharmaceutical dosage form consists essentially of an extract of *Curcuma longa* rhizome and a carrier; wherein said *Curcuma longa* rhizome extract is prepared by the following steps:
    (a) washing *Curcuma longa* rhizomes in distilled water, removing most of the rhizome skin, cutting said rhizome into pieces, drying said cut rhizomes at 40-42° C. and powdering said dry, cut rhizomes to obtain powdered rhizome;
    (b) combining the powdered rhizomes of part (a) with 40% ethanol to create a mixture;
    (c) stirring the mixture of part (b) for 20 hours at room temperature to create a stirred mixture,
    (d) centrifuging the stirred mixture of part (c) to create insoluble material and a clear, soluble extract, (e) removing the insoluble material from the clear, soluble extract and collecting said clear, soluble extract;

wherein the clear, soluble extract of part (e) is the extract of *Curcuma longa* rhizome;

wherein said pharmaceutical dosage form is selected from the group consisting of a tablet, a coated tablet, a capsule and an emulsion;

wherein the carrier is selected from the group consisting of magnesium carbonate, magnesium stearate, talc, sugar, lactose, pectin, dextrin, starch, gelatin, methylcellulose, sodium carboxymethylcellulose, cocoa butter, a colorant, a flavor, a stabilizer, a buffer, a sweetener, a dispersant, a thickener, a solubilizing agent and mixtures thereof;

and wherein in part (b), the powdered rhizome and 40% ethanol are combined in a ratio of 1:5 to 1:100 (powdered rhizome: 40% ethanol).

2. The method of claim 1, wherein said pharmaceutical dosage form contains about 5% to about 95% of said *Curcuma longa* rhizome extract.

3. The method of claim 1, wherein the powdered rhizome and 40% ethanol are combined in a ratio of 1:20 to 1:80 (powdered rhizome: 40% ethanol).

4. The method of claim 1, wherein the powdered rhizome and 40% ethanol are combined in a ratio of 1:30 to 1:50 (powdered rhizome: 40% ethanol).

5. The method of claim 1, wherein the powdered rhizome and 40% ethanol are combined in a ratio of 1:40 (powdered rhizome: 40% ethanol).

6. The method of claim 1, wherein the subject is a mammal.

7. The method of claim 6, wherein the mammal is selected from the group consisting of cattle, pigs, sheep, chicken, turkey, buffalo, llama, ostrich, dogs, cats, and humans.

8. The method of claim 7, wherein the mammal is a human.

\* \* \* \* \*